United States Patent [19]

Morrow et al.

[11] Patent Number: 5,342,780

[45] Date of Patent: Aug. 30, 1994

[54] METHODS OF ENZYMATICALLY SEPARATING STEREOISOMERS OF A RACEMIC MIXTURE OF A REACTIVE ESTER

[75] Inventors: Cary J. Morrow; Joe S. Wallace, both of Albuquerque, N. Mex.

[73] Assignee: University of New Mexico, Albuquerque, N. Mex.

[21] Appl. No.: 940,129

[22] Filed: Sep. 3, 1992

Related U.S. Application Data

[62] Division of Ser. No. 470,670, Jan. 26, 1990, abandoned.

[51] Int. Cl.$^5$ .................... C07C 67/00; C12P 7/62; C12N 9/20
[52] U.S. Cl. ............................ 435/280; 435/135; 435/198
[58] Field of Search ................... 435/135, 280, 198

[56] References Cited

U.S. PATENT DOCUMENTS

| | | | |
|---|---|---|---|
| 2,950,313 | 8/1960 | Kirkpatrick . | |
| 4,022,808 | 5/1977 | Yoshihara et al. | 554/149 |
| 4,921,798 | 5/1990 | Boaz | 435/146 |
| 4,963,492 | 10/1990 | Keller et al. | 435/280 |
| 5,032,523 | 7/1991 | Amano et al. | 435/280 |
| 5,108,916 | 4/1992 | Cobbs et al. | 435/135 |

FOREIGN PATENT DOCUMENTS 61-189248  8/1986  Japan .

OTHER PUBLICATIONS

Wallace et al. (1989) ACS Meeting Abstract 198, in Biosis BR 37:107965, meet date Sep. 10–15, 1989.
Cambou, B. and Klibanov, A. M., *J. Am. Chem. Soc.*, 106:2687 (1984).
Zaks, A. and Klibanov, A. M., *Science*, 224:1249 (1984).
Cambou, B. and Klibanov, A. M., *Biotechnology and Bioengineering*, XXVI:1449 (1984).
Mohr et al., *Helv. Chim. Acta*, 70:142 (1987).
Mohr et al., *Tetrahedron Letters*, 1989, 30:19, pp. 2513–2516.
Bianchi et al., *J. Org. Chem.*, 53:104 (1988).
Wallace et al, (1990) *J. Org. Chem.*, 55, 3544–3546.
Bradbury et al, (1978), *Carb. Res.*, 60, 183–186.
Ogata et al, (1978), *Polymer J.*, 10(5), 499–504.
Scilimati et al, (1988), *Tetrah. Lett.*, 29(39), 4927–4930.
Burns et al, (1989), *J. Org. Chem.*, 54, 2826–2834.
Coffen et al, (1989, Aug. 2), EP 325,971, in *Chem Abst.*, 112, p. 500, Abst #215248.
Mislow (1985), "Introduction to Stereochemistry", W. A. Benjamin, Inc., Menlo Park, pp. 93–94.

*Primary Examiner*—Douglas W. Robinson
*Assistant Examiner*—Jon P. Weber
*Attorney, Agent, or Firm*—Lowe, Price, LeBlanc & Becker

[57] ABSTRACT

Methods of separating stereoisomers of a racemic mixtures of a compound employ porcine pancreatic lipase which selectively transesterfies one enantiomer of an ester function which is proximate to a chiral isomeric site are presented. The compound is a reactive ester of the formula:

$$R^1-\overset{\overset{\displaystyle O}{\|}}{C}-R-CH(-R^2)(-R^3).$$

The method comprises obtaining a racemic mixture of the reactive ester, reacting the reactive ester with a poly(ethylene glycol) of average molecular weight of about 100 to about 10,000 Daltons and the enzyme. The reactive ester, the poly(ethylene glycol) and the enzyme are reacted in a medium in proportions other conditions effective to form a chiral site proximate poly(ethylene glycol) ester. The chiral site approximate poly(ethylene glycol) ester is then separated from the reaction medium, the reactive ester, the poly(ethylene glycol) and the enzyme.

8 Claims, No Drawings

METHODS OF ENZYMATICALLY SEPARATING STEREOISOMERS OF A RACEMIC MIXTURE OF A REACTIVE ESTER

This application is a division of application Ser. No. 07/470,670 filed Jan. 26, 1990 now abandoned.

TECHNICAL FIELD

This invention relates to the resolution of enantiomers by stereospecific enzymatic transeseterification of an ester function placed up to 2 C-atoms away from a chiral center and separating the two stereoisomers based on their different physicochemical properties.

BACKGROUND ART

The resolution of enantiomers by enantioselective hydrolysis with an enzyme is known. However, the recent discovery that many hydrolytic enzymes work well in low polarity organic solvents (Cambou, B. and Kilbanov, A. M. *J. Am. Chem. Soc.*, 1984, 106, 2687; Zaks, A., and Kilbanov, A. M., *Science*, 1984, 224, 1249) has allowed for enzymatic resolution to be extended to new reactions such as esterification (Cambou, B. and Kilbanov, A. M., *Biotechnology and Bioengineering*, 1984, XXVI, 1449), and transesterification (Cambou, B. and Kilbanov, A. M., *J. Am. Chem. Soc.*, 1984, 106, 2687; Cambou, B. and Kilbanov, A. M., *Biotechnology and Bioengineering*, 1984, XXVI, 1449).

Resolution by enzymatic transesterification solves some of the problems associated with enzymatic hydrolyses. Among these are the low solubility of many organic compounds in water, the difficulty of recovering the enzyme for reuse, and the requirement for adjusting the ph as the reaction progresses. Moreover, an increase in enzyme stability has been reported when it is used in an organic solvent and higher reaction temperatures are tolerated (Zaks, A. and Kilbanov, A. M., *Science*, 1984, 224, 1249).

The resolution of a racemic mixture of esters may be carried out by transesterifying one enantiomer of a racemic ester with an achiral alcohol (Cambou, B. and Kilbanov, A. M. *Biotechnology and Bioengineering*, 1984, XXVI, 1449). More commonly, however, one enantiomer of a racemic alcohol transesterifiers and achiral ester. (Cambou, B. and Kilbanov, A. M., *J. Am. Chem. Soc.*, 1984, 106, 2687; Cambou, B. and Kilbanov, A. M., *Biotechnology and Bioengineering*, 1984, XXVI, 1449). The latter case, which is useful for resolving alcohols, leads to the necessity for separating an ester from an alcohol. The first case, which is useful for resolving racemic mixtures of esters, leaves both enantiomers in the form of esters. The separation of the isomers in most cases requires tedious chromatography or careful distillation. (Cambou, B. and Klibanov, A. M., *Biotechnology and Bioengineering*, 1984, XXVI, 1449). This has been a substantial drawback which accounts for the limited application of this technology up to the present time.

The resolution of 3,4'-epoxybutyrate by stereoselective enzymatic hydrolysis of its methyl or other alkyl esters was recently reported by Mohr et al. (Mohr et al., *Helv. Chim. Acta.*, 1987, 70, 142; Mohr et al., *Tetrahedron Letters*, 1989, 30 (19(, 2513) and by Bianchi et al. (Bianchi et al., *J. Org. Chem.*, 1988, 53, 104)). Mohr et al. hydrolyzed a methyl ester with pig liver esterase and obtained the unchanged (R) ester and the (S) acid. However, the enantiomeric excesses of each compound after separation was not very high. Bianchi et al., supra, conducted the reaction with 13 different enzymes and concluded that porcine pancreatic lipase (PPL) provides the best stereoselectivity when alkyl, e.g., butyl, isobutyl and octyl, esters are hydrolyzed.

DISCLOSURE OF THE INVENTION

This invention relates to a compound of the formula

wherein

R is $(C_0-C_2)$alkyl or $-O(C_0-C_2)$alkyl, all of which may be further substituted with $(C_1-C_4)$alkyl;

$R^1$ is selected from the group consisting of —OH, —O$(C_1-C_{15})$alkyl or alkenyl, —O—$(C_3-C_{15})$cycloalkyl, cycloalkenyl, cycloalkynyl and —O—$(C_4-C_{22})$aryl, all of which may contain N, S or O in the chain or ring structure and be further substituted with one or more $(C_1-C_4)$alkyl, OH, $NO_2$ or halogen, and $R^1$ is preferably $CF_3CH_2O$, $CCl_3CH_2O$, $ClCH_2CH_2O$ or

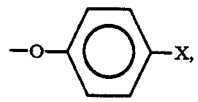

wherein X is Cl, $NO_2$ or F;

$R^2$ is selected from the group consisting of $(C_1-C_{12})$alkyl, alkenyl or alkynyl, $(C_3-C_{15})$cycloalkyl, cycloalkenyl, cycloalkynyl, $(C_4-C_{22})$aryl and $(C_5-C_{23})$alkylaryl or arylalkyl, all of which may be substituted in the ring or chain with O, N or S; and $R^3$ is selected from the group consisting of $R^2$, OH, $NH_2$, $OR^2$, $NHR^2$, $NR^2$, $SR^2$, $O(C_1-C_6)$acyl or aroyl, $NH(C_1-C_6)$acyl or aroyl, —CH($R^2$)-(R—$COR^1$) and halogen, wherein $R^2$ is different from $R^3$;

or $R^2$ and $R^3$ form a ring selected from the group consisting of $(C_3-C_{15})$cycloalkyl, cycloalkenyl or cycloalkynyl, $(C_4-C_{22})$aryl, and $(C_5-C_{23})$alkylaryl or arylalkyl, all of which may be further substituted in the ring or chain with N, S or O, said compound being selected from the group consisting of the stereoisomers thereof in substantially stereochemically pure form.

Also disclosed herein are polymers of the formula

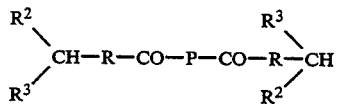

wherein

R is $(C_0-C_2)$alkyl or $-O(C_0-C_2)$alkyl, all of which may further be substituted with $(C_1-C_4)$alkyl;

P is a poly(alkylene glycol) of the formula —O—$(-(CH_2)_n-O)_x-$, wherein n is 1 to 10 and x is 1 to 1,000; and $R^2$, $R^3$ and R are as disclosed above.

Also disclosed herein are polymers of the formula

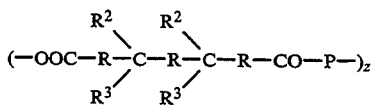

wherein
R is $(C_0-C_2)$alkyl;
$R^2$ is H or is as described above; and
$R^3$ is as described above but different from $R^2$, and
P is a poly alkylene glycol of the formula $-O-(-(CH_2)_n-O)_x-$, wherein n is 1 to 10 x is 1 to 10,000 and z is 1 to 10,000.

This invention also relates to a method of separating the isomers of a racemic mixture of the compound of the invention, which method comprises
obtaining a racemic mixture of an ester of the formula $R^4-OC-R-CH(-R^2)(-R^3)$, wherein R, $R^2$, and $R^3$ are as described above, and $R^4$ is $O(C_1-C_6)$alkyl or $O(C_4-C_{10})$aryl, and preferably $-OCH_2CX_3$ or $O(C_4-C_{10})$aryl, all of which may be substituted with O or S and/or in the ring with halogen $NO_2$ or $OCH_2CX_3$, wherein X is halogen;
reacting the reactive ester with a poly(ethyleneglycol) of average molecular weight about 150 to 20,000 daltons and an enzyme capable of enantioselectively transesterifying an ester function which is proximate to an (S) (or (R))chiral isomeric site; the reactive ester, the poly(ethylene glycol) and the enzyme being reacted in a medium, in proportions and under conditions effective to form a chiral site proximate poly(alkyleneglycol) ester of one enantiomer of the ester; and
separating the chiral site proximate poly(alkyleneglycol) ester(s) from the reaction medium, the unchanged enantiomer of the reactive ester, the enzyme and, subsequently, the poly(alkyleneglycol).

A method of preparing polymers of the formula

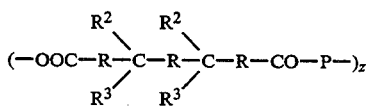

comprising
obtaining a reactive diester of the formula

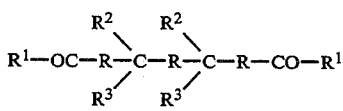

wherein R, $R^1$, $R^2$, and $R^3$ are as defined above;
reacting the reactive diester with a poly(alkylene glycol) of the formula $HO((CH_2)_n-O-)H_xH$ of average molecular weight about 150 to 20,000 daltons and an enzyme capable of enantioselectively transesterfying an ester function which is proximate to a pair of chiral isomeric sites; the reactive ester, poly(alkylene glycol) and the enzyme being reacted in a medium, in proportions and under conditions effective to form a bis chiral site proximate polyester between the diol and one stereoisomer of the diester.

A more complete appreciation of the invention and many of the attended advantages thereof will be readily perceived as the same becomes better understood by reference to the following detailed description. Other objects, advantages and features of the present invention will become apparent to those skilled in the art from the following discussion.

BEST MODE FOR CARRYING OUT THE INVENTION

This invention arose from a desire to improve the ease of separating two stereoisomeric esters while retaining advantages associated with the known enzyme-catalyzed transesterification in an organic medium. The present invention is an improvement over the method disclosed by Mohr, et al, supra, Bianchi et al., supra, Klibanov et al, supra, and Mohr et al, supra, and it relies, inter alia, on a combination of stereospecific enzyme transesterification with a polymeric alcohol of predetermined characteristics and the separation of the stereoisomers by relying on different physicochemical characteristics of the compounds.

The alcohol which is utilized herein is of a polymeric nature and has a molecular weight range suitable for imparting to the transesterified isomer properties which are substantially different from those of the untransesterified stereoisomer. The polymeric alcohol utilized for the transesterification must have low solubility in the reaction solvent. In this manner, the transesterified stereoisomer, by taking on the characteristics of the polymeric alcohol, becomes insoluble and easily separable from the unchanged isomer by known separation techniques. After the stereoisomer transesterified with the insoluble polymer alcohol is separated from the reaction mixture, the unmodified stereoisomer may be isolated by evaporating the solvent or other known separation techniques such as distillation, extraction into a solvent, and the like. The insoluble transesterified ester may be hydrolyzed or again transesterified by chemical or enzymatic catalysis to thereby obtain the free acid or a low molecular weight alcoholic ester thereof.

This invention therefore provides stereochemically pure esters containing at least one chiral center, where the chiral center is positioned up to 2 C-atoms away from the carboxyl moiety. The compounds of the invention have the formula

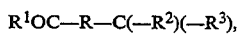

wherein
R is $(C_0-C_2)$alkyl or $-O(C_0-C_2)$alkyl, which may be further substituted with $(C_1-C_4)$alkyl;
$R^1$ is selected from the group consisting of $-OH$, $-O(C_1-C_{15})$alkyl or alkenyl, and $O(C_3-C_{15})$cycloalkyl, cycloalkenyl, cycloalkynyl, $O(C_4-C_{22})$aryl and $O(C_5-C_{23})$alkylaryl or arylalkyl, all of which may contain N, S, or O in the chain or ring structure and be further substituted with one or more $(C_1-C_4)$alkyl, OH, $NO_2$ or halogen;
$R^2$ is selected from the group consisting of $(C_1-C_{12})$alkyl, alkenyl or alkynyl, $(C_3-C_{15})$cycloalkyl, cycloalkenyl or cycloalkynyl, $(C_4-C_{22})$aryl, and $(C_5-C_{23})$alkylaryl or arylalkyl, all of which may be substituted in the ring or chain with O, N or S; and
$R^3$ is selected from the group consisting of $R^2$, OH, $NH_2$, $OR^2$, $NHR^2$, $SR^2$, $O-(C_1-C_6)$aryl, $NH-(C_1-C_6)$ acyl, $-CH(R^2)(-R-COR^1)$ and halogen, wherein $R^2$ is different from $R^3$;
or $R^2$ and $R^3$ form a ring selected from the group consisting of $(C_3-C_{15})$cycloalkyl, alkenyl or alkynyl, $(C_4-C_{22})$aryl and $(C_5-C_{23})$alkylaryl or arylalkyl, all of which may be further substituted in the ring or chain with N, S or O, said compound being selected from the group consisting of the isomers thereof in substantially stereochemically pure form.

$R^1$ is preferably $CF_3CH_2O$, $CCl CH_2O$, $ClCH_2CH_2O_2$ or

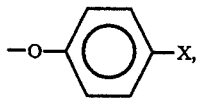

wherein X is Cl, $NO_2$ or F.

The substantially stereospecifically pure compounds of the invention have about 95% or greater purity, and in some cases up to about 97% or greater purity. These stereoisomers are, in a most preferred embodiment, substantially devoid of detectable amounts of other isomers of the same compound.

A particularly preferred group of stereoisomers is that having the (R) configuration. Another particularly preferred group is that having the (S) stereochemical configuration. Other preferred groups are those where R is held by a single bond, and where R is $C_1$-alkyl. Preferred groups are also those wherein $R^1$ is OH or a poly(alkylene glycol) having a molecular weight of about 100 to 20,000 daltons, and more preferably about 1000 to 5,000 daltons. Also preferred are those wherein $R^2$ is H or an aliphatic hydrocarbon. Other preferred groups are those wherein $R^2$ is aryl or a cycloaliphatic residue.

Still other preferred groups of compounds are those where $R^3$ is $R^2$, $OR^2$, or $-CH(-OR^2)(-R-COOR^1)$ and the like as described above, as long as $R^2$ is different from $R^3$. Another preferred group is that where $R^2$ and $R^3$ form a ring structure such as a cycloaliphatic or aromatic ring, optionally containing N, S or O.

The group of compounds where $R^3$ is $-CH)-OR^2-)(-R-COOR^1)$ have at least two chiral centers and the method of the invention may be applied to separate all stereoisomers from one another by itself or in combination with the method of the co-filed application by the present inventors entitled "Substantially Pure Stereoisomers and Method of Preparation", the entire contents of which are incorporated herein by reference.

A particularly preferred group of stereochemically pure compounds is that having more than one chiral center in the molecule. These compounds are obtained as racemic mixtures of the (R,R), (R,S), and (S,S) stereoisomers thereof. These stereoisomers may be separated from one another by a repetitive application of the method of the invention.

The compounds of the invention may be prepared by the method disclosed herein or by any other known method. The present method, however, permits the large-scale high stereochemical purity preparation of these compounds.

The stereochemically pure compounds of the invention are suitable for the preparation of polymers which have non-linear optical properties, as components of catalysts for making optically active compounds or as media for the separation of optically active compounds. Examples of such polymers are helical polymers having a single screw sense. The pitch and period of the helical polymers can be adjusted by varying the structure of the alcoholic stereoisomer utilized. The nitrogen-containing compounds also permit binding of metals to the helix to make chiral catalysts.

The polymers of the invention may be any polymer formed by random, block or alternate binding of the present chiral ester stereoisomers of the invention with other bridging structures. By means of example, the polymer of the invention may have the general formula

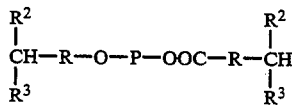

wherein
R is $(C_0-C_2)$alkyl or $-O(C_0-C_2)$alkyl, which may further be substituted with $(C_1-C_4)$alkyl;
P is a poly(alkylene glycol) of the formula $-O-((CH_2)_n)_x$, wherein n is 1 to 10 and x is 1 to 10,000; and
R, $R^2$ and $R^3$ are as disclosed above.

Also disclosed herein are are polymers of the formula

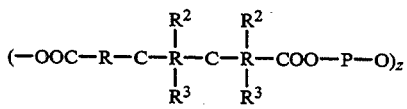

wherein
R is $(C_0-C_2)$alkyl;
$R^2$ is H or is as described above;
$R^3$ is as described above but different from $R^2$; and
P is poly(alkylene glycol) of the formula $-O-(-(CH_2)_n-O)_x$, wherein n is 1 to 10, x is 1 to 10,000, and z is 1 to 10,000.

The polymers of the invention may be prepared by the method of the invention by reaction of an excess of a racemic mixture of the stereoisomeric chiral compound of the invention described above with a diol of the formula $HO((CH_2)_n-O-)_xH$ in the presence of an enzyme capable of stereoselectively transesterifying one enantiomer of the chiral compound with the diol at each end, two molecules of the chiral compound being required to completely transesterify both alcoholic functions of each diol molecule. The reaction is conducted in a medium, in proportions of the reactants and under conditions effective to form a bis site proximate polyester between the diol and one stereoisomer of the diester.

Also part of this invention is a method of separating the stereoisomers of a racemic mixture of the compounds of the invention comprising
obtaining a racemic mixture of a reactive ester of the formula $R^1-OC-R-CH-(R^2)(-R^3)$, wherein R, $R^2$, and $R^3$ are as described above, and $R^1$ is $O(C_1-C_6)$alkyl, $-O-Ar$, $-OCH_2CH_2X$ or $-OCH_2CX_3$, wherein X is halogen and the Ar may further contain N, S or O in the ring structure and;
reacting the reactive ester with a poly(ethylene glycol) or diol terminated polyether of average molecular weight about 100 to 20,000 daltons under conditions effective to form the poly(ethyleneglycol) or poly ether alcohol ester of one enantiomer of the ester; and
separating the chiral site proximate poly(ethylene glycol) ester(s) from the reaction medium, the reactive ester, and the enzyme and subsequently from the poly(ethylene glycol).

The racemic mixtures of a reactive ester as described above are either commercially available or may be prepared by methods known in the art. For example, this may involve taking a mixture of a chiral acid and treating it with excess alcohol in the presence of an acid catalyst or with a dehydrating agent such as dicyclohexyl carbodiimide (DCC) in the presence of a catalyst such as 4-(N,N dimethylamino)pyridine (DMAP) as described by Hassner and Alexanian (Hassner and Alexanian, Tetrahedron Lett., 1978, 4475).

The racemic mixture of the reactive ester is reacted with a poly(ethylene glycol) of average molecular weight about 100 to 20,000 daltons, more preferably about 500 to 10,000, and still more preferably about 1,000 to 5,000 daltons. This reaction is conducted in the presence of an enzyme capable of stereoselectively transesterifying one enantiomer of an ester function which is proximate to a chiral site. The reactants are provided in a liquid medium, preferably an anhydrous organic compound which acts as a solvent for the ester substrate but not the poly(ethylene glycol) and also preferably under e.g., a non-oxidizing atmosphere. The non-aqueous conditions under which the transesterification step is conducted are advantagous because most organic esters are far more soluble in organic solvents than in water. The solubility of the substrate ester is, therefore, ensured while the transesterified poly(ethylene glycol) ester resulting from the transesterification is insoluble and their separation is easily obtained.

The enzyme may also be recovered or separated from an organic solvent in a far more simple manner than it is from an aqueous medium. In addition, the non-aqueous enzymatic reaction has the advantage that no acidic product is formed and therefore, the pH of the reaction need not be adjusted as the reaction progresses.

The enzyme transesterification reaction is conducted at a temperature of about 10° to 75° C., more preferably about 25° to 60° C., and more preferably 35° to 50° C. This is a range of temperatures within which the reaction proceeds well and the poly(ethylene glycol) stays in the liquid state.

The method of the invention thus permits the resolution of one enantiomer of a racemic mixtures of esters by transesterication of one enantiomer of the mixture with an achiral alcohol followed by cooling to cause separation of the transesterified enantiomer from the reaction mixture. Prior art methods for separation of racemic ester mixtures by enzyme-catalyzed transesterification required the subsequent separation of one stereoisomer from another by somewhat cumbersome methods such as distillation or chromatography. This probably accounts for their limited application, particularly, their lack of suitable adaptation to large-scale preparation.

The alcohol utilized as a substrate for the transesterification reaction is sufficiently large and its properties thus dominate those of the chiral acyl residue to which it is bound. The alcohol is insoluble in the reaction solvent and the ester product (the transesterified product) also has low solubility in the reaction solvent. This allows for an easy removal of the transesterified ester enantiomer from the unchanged ester enantiomer by simple filtration, decantation or centrifugation.

Particularly preferred organic solvents are symmetrical and unsymmetrical aliphatic ethers, aliphatic hydrocarbons, aromatic hydrocarbons, alkyl halides, arylalkyl ethers and aryl halides, among others. However, any other organic solvents which act as such for the reactive ester isomer while permitting that the transesterified esters precipitate or otherwise separate are suitable.

The reaction of the reactive ester substrate with the polyalkylene glycol and the enzyme is preferably conducted in proportions of about 1 mmol:10 mmol:2.5 g to 1 mmol:0.5 mmol:0.05 g, more preferably about 1 mmol:5 mmol:1.0 to 1 mmol:0.6 mmol:0.1 g, and still more preferably about 1 mmol:1 mmol:0.5 g to 1 mmol:0.7:0.2 g.

The separation step is conducted at a temperature where the poly(ethylene glycol) and the poly(ethylene glycol) ester(s) are in solid form or in liquid form, but having low solubility in the reaction solvent. A particularly appropriate temperature range may be found for the separation of each specific poly(ethylene glycol)-/solvent combination utilized and is in general lower than the temperature utilized for the enzymatic reaction. Typically, the separation temperature is less than about 30° C., and in some instances less than about 20° C., and for lower molecular weight poly(alkylene glycols), it may be less than about 5° C. An artisan would know how to find appropriate temperature ranges for various molecular weight PEGs without undue experimentation. This separation step is suitable for separating the reactive ester and the reaction medium from the enzyme, the poly(ethylene glycol) and the poly(ethylene glycol) ester(s). What remains in the organic medium is the reactive ester of the unchanged enantiomer while the enzyme, the poly(ethylene glycol) and the poly(ethylene glycol) ester(s) precipitate out of the medium.

Thereafter, the poly(ethylene glycol) and the poly(ethylene glycol) ester(s) are separated from the enzyme by extraction with a solvent for the poly(ethylene glycol) and the poly(ethylene glycol) ester(s). Typically, solvents that may be utilized herein are dichloromethane, chloroform, and tetrahydrofuran. However, any other solvent for the poly(ethylene glycol) and the poly(ethylene glycol) ester(s) that is not a solvent for the enzyme is suitable.

After separating the enzyme from the solution, the poly(ethylene glycol) may be separated from the ester(s) being resolved by converting the latter to the corresponding soluble alkyl ester(s), placing the mixture under conditions effective for the poly(ethylene glycol) to form a separate, preferably solid phase, and separating the poly(ethylene glycol) from the alkyl ester(s) which is soluble in the extraction solvent.

Suitable conditions for converting the poly(ethylene glycol) ester(s) to the corresponding ($C_1$-$C_4$) alkyl ester(s) are the reaction of the poly(ethylene glycol) ester(s) with an alkyl alcohol in a proportion of about 1 mmol:200 mmol to 1 mmol:1 mmol, more preferably about 1 mmol:100 mmol to 1 mmol:5 mmol, and still more preferably about 1 mmol:30 mmol to 1 mmol:15 mmol in a alkaline or acidic medium at a acidity equivalent to about pH 2.0 and a temperature of about 25° C. to 60° C.

The poly(ethylene glycol) ester may be mixed with stirring in a suitable alkyl alcohol such as methanol in the proportions specified above. A catalytic amount of base such as sodium methoxide or an acid such as concentrated sulfuric may be added to the solution and the mixture stirred, e.g., at room temperature until no further reaction is observed. The alkyl ester product may be isolated by reducing the reaction mixture to almost dryness and extracting the residue with an appropriate organic solvent such as isopropyl ether. The ether phase may then be evaporated to yield the alkyl ester.

The conditions for the separation of the poly(ethylene glycol) from the ester(s) remaining in solution encompass lowering the temperature, permitting the poly(ethylene glycol) to precipitate or separate from the solution and, without varying the temperature, centrifuging and, if necessary, then filtering or decanting the solution away from the separated poly(ethylene glycol) phase. These are all techniques known in the art which need not be further described herein.

In a particularly preferred embodiment of the method, the poly(ethylene glycol) ester(s) is converted to the corresponding soluble ($C_1$–$C_4$)alkyl ester(s) by adding thereto a ($C_1$–$C_4$)alkanol and a transesterifying enzyme in a medium under conditions effective to form the corresponding alkyl ester(s).

In another preferred embodiment of the invention, the method further comprises subjecting a partially stereo-chemically pure reactive ester(s) separated from the chiral site proximate poly(ethylene glycol) ester(s) to another reaction step to form further chiral site proximate poly(ethylene glycol) ester(s) by transesterification with poly(ethylene glycol) of any previously unreacted chiral site proximate reactive ester having the stereochemistry preferred by the enzyme, and then separating the new chiral site proximate poly(ethylene glycol) ester(s) from the reaction medium, the reactive ester(s), the enzyme, and, subsequently, the poly(ethylene glycol).

The conditions for conducting these steps are similar to the ones described above. However, an artisan would know how to vary different parameters in order to attain further conversion of one enontiomer of the reactive substrates into the products if necessary.

In still another preferred embodiment of the invention, the method further comprises separating the reactive ester and the reaction medium from the enzyme, the poly(ethylene glycol) and the poly(ethylene glycol) ester(s) at a temperature where the poly(ethylene glycol) and the poly(ethylene glycol) ester(s) are in solid form and then separating the reactive ester(s) from the reaction medium. The reactive ester recovered in this manner is substantially in the form of one enantiomer of the reactive ester(s) which is substantially free from the other enantiomer.

The temperature at which the unchanged reactive ester and the reaction medium are separated from the enzyme, the poly(ethylene glycol) and the poly(ethylene glycol) ester(s) is as described above. Typically, the temperature is about −70° to 100° C., and more preferably about −10° to 30° C. Other conditions for the separation steps are generally as described above.

The reactive ester may be separated from the reaction medium by methods known in the art such as evaporation of the medium, distillation and the like. This technology is substantially known and will not be described in further detail herein.

In a most preferred embodiment of the method, the enzyme utilized for the transesterification step is porcine pancreatic lipase. This enzyme has been found, in many instances, to provide the best stereospecificity for the transesterification reaction.

As already indicated, the racemic mixture of the reactive ester may be subjected more than one time to the present method.

The method of the invention will be exemplified by reference to 2,2,2-trichloroethyl-3,4-epoxybutanoate and its transesterification with poly(ethylene glycol). This reaction is shown in the following Scheme.

Stereoselective Porcine Pancreatic Lipase Catalyzed Transesterification of 2,2,2-Trichloroethyl (')-3,4-Epoxybutanoate by Poly(ethylene glycol)

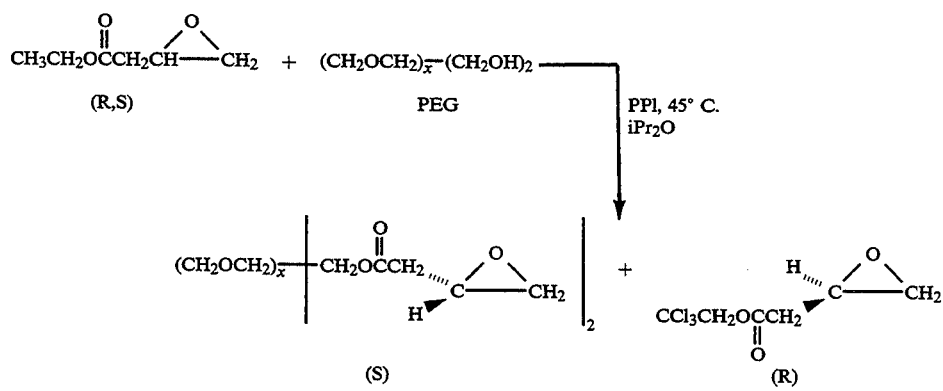

Having now generally described this invention, the same will be better understood by reference to certain specific examples, which are included herein for purposes of illustration only and are not intended to be limiting of the invention or any embodiment thereof unless so specified.

EXAMPLES

EXAMPLE 1

Selective transesterification of 2,2,2-trichloroethyl (S)-3,4-epoxybutanoate.

The (S)-enantiomer from racemic 2,2,2-trichloroethyl (R,S)-3,4-epoxybutanoate, ((R,S) compound 1), was selectively transesterified by low molecular weight (about 1500 Daltons) polyethylene glycols (PEG) using porcine pancreatic lipase (PPL) as the catalyst. The reaction required about 5 hours to consume one-half of the racemic ester at 45° C., a temperature capable of keeping the PEG as a molten phase in diisopropyl ether.

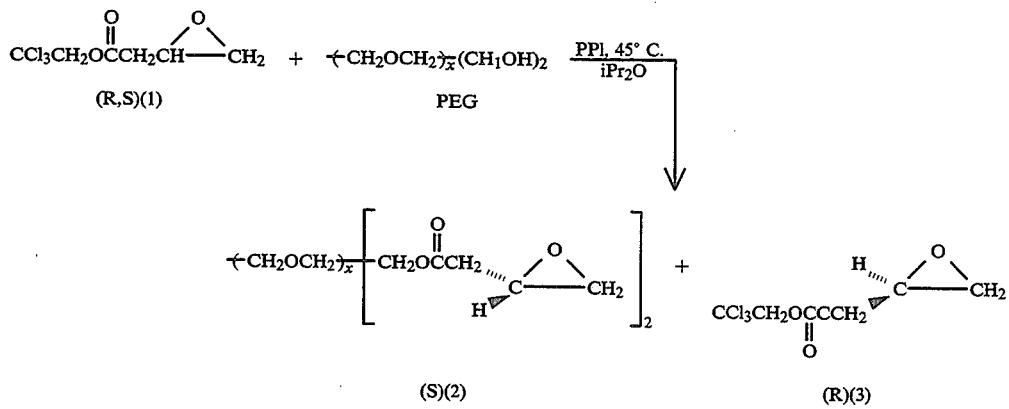

(R,S)(1)  PEG  (S)(2)  (R)(3)

The separation of the PEG (S)-ester, (compound (S)-2), from the unchanged compound (R) 1 was achieved by cooling the reaction mixture to 0° C. and filtering off the enzyme and the solidified compound 2. The (R)-enantiomer was isolated in high yield and high enatiomeric excess by evaporating the solvent from the filtrate. The PEG ester of the (S)-enantiomer (compound(S)-2), was recovered by extracting it into methylene chloride and filtering off the catalyst.

The structure and enantiomeric purity of the (R) 1 compound was proven by its conversion to the corresponding (−)-carnitine chloride (compound 3). This was done by enzymatic hydrolysis of the trichloroethyl ester followed by treatment with trimethylamine and acidification with HCl as described by Bianchi, et al. (Bianchi, D. et al, supra)

The carnitine displayed a rotation $[\alpha]_D -22.9°$ corresponding to an enantiomeric excess of >96% by comparison with the literature value of $[\alpha]_D -23.7°$ for the natural product. (Strack, E., Lorenz, J., Z. Physiol. Chem, 1960 318, 129).

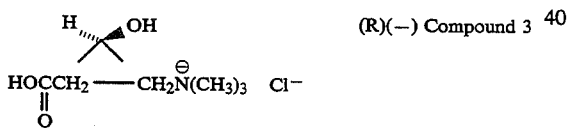

(R)(−) Compound 3

Resolution of a racemic mixture of 3,4-epoxybutyrates by enantioselective, enzymatic hydrolysis of the methyl or other alkyl esters has recently been reported by Mohr et al. (Mohr, P.; Rosslein, L.; Tamm, C., Helv. Chim. Acta., 1987, 70, 142) and by Bianchi et al. (Bianchi et al., supra). In the former, the methyl ester was hydrolyzed with pig liver esterase to give a 40% recovery of the unchanged (R)-ester and a 30% yield of the (S)-acid. An ee of 97% was found for the derivative prepared from the acid though it may have been improved by recrystallization. The derivative prepared from the unchanged (R)-ester indicates an ee of 82%. Though supported by theory (Chen, C. S.; Fujimoto, Y.; Girdaukas, G.; Sih, C. J., J. Am. Chem. Soc., 1982 104, 7294) the author's statement that a high ee for either enantiomer can be achieved by stopping the reaction after 40% reaction or after 60% reaction was not proven experimentally.

A survey of 13 different enzyme preparations reported by Bianchi, et al., supra, led to the conclusion that PPL (steapsin) provided the best enantioselectivity when alkyl (particularly butyl, isobutyl, and octyl) esters were hydrolyzed. However, to achieve an ee of >95% for the unchanged (R)-ester, it was necessary to hydrolyze 60–70% of the starting material.

The (S)-enantiomer compound (S)-2 was further converted to the corresponding methyl ester by PPL catalyzed transesterification with methanol. Based on the rotation of +10.6° reported (Mohr, P.; Rosslein, L.; Tamm, C.; Helv. Chim. Acta. 1987, 70, 142) for methyl-(R)-3,4-epoxybutanoate corresponding to an ee of 82%, the rotation of −11.61° observed herein for the (S)methyl ester that is isolated from the PEG by transesterification would correspond to an ee of 89%.

EXAMPLE 2

Preparation of 2,2,2-trichloroethyl 3-butenoate 8.130 g (95.0 mmol) of vinylacetic acid were dissolved in 50 mL of methylene chloride and treated successively with 14.34 g (96.0 mmol) of 2,2,2-trichloroethanol and 0.40 g (3.3 mmol) of 4-(dimethylamino)-pyridine (DMAP) following the general method of Hassner and Alexanian (Hassner, A.; and Alexanian, V., Tetrahedron Lett., 1978, 4475).

The mixture was then cooled to 0° C. After 15 min., 19.81 g (96.0 mmol) of dicyclohexylcarbodiimide (DCC) and 25 mL of methylene chloride were added with stirring. A white precipitate was observed to form immediately.

When the DCC addition was complete, the mixture was allowed to warm to ambient temperature and remain there for two days. The precipitate was then filtered off and the filtrate washed successively with three portions of a saturated solution of citric acid, two portions of saturated aqueous sodium bicarbonate, and one portion of saturated brine.

After drying over magnesium sulfate, the solvent was evaporated to give a light yellow oil. The oil was passed through a 4-inch column of silica (Merck Grade 60/60 Angstrom) and eluted with methylene chloride to obtain 18.45 g (89.3%) of a colorless liquid that was shown by VPC to be >95% pure.

$^1$H NMR (CDCl$_3$): δ3.25 (d of t,J=6.9, 1.4 Hz, 2H), 4.76 (s, 2H), 5.25 (m, 2H), 5.95 (m, 1H);

$^{13}$C NMR (CDCl$_3$): δ169.8, 129.0, 119.3, 95.0, 73.9, 38.5.

EXAMPLE 3

Preparation of 2,2,2-trichloroethyl (R,S)-3,4-epoxybutanoate ((R,S) (1))

10.0 g of 2,2,2-trichloroethyl-3-butenoate were dissolved in 50 mL of methylene chloride and treated with 11.1 g (~1.4 equiv.) of m-chloroperoxybenzoic acid in 100 mL of methylene chloride following the general method of Dahill et al. (Dahill, R. T.; Dorsky, J.; Easter, W., *J. Org. Chem.* 1970, 35, 251). The reaction was allowed to continue for 3 days at ambient temperature after which time VPC analysis showed the starting alkene to have been consumed.

The mixture was then cooled in an ice bath and a saturated sodium sulfite solution added with stirring until a KI starch test was negative. The m-chlorobenzoic acid which precipitated during the reaction was filtered off and the filtrate washed with three portions of the aqueous sodium sulfite solution, two portions of saturated aqueous sodium bicarbonate, and one portion of saturated brine.

After drying over magnesium sulfate, the solvent was evaporated and the oily product purified by distillation in vacuo.

B.P. 65°–70° C. 0.1 mm.

$^1$H NMR (CDCl$_3$): $\delta$2.59 (d of d, J=4.8, 2.6 Hz, 2H), 2.72 (d, J=5.79 Hz, 2H), 2.86 (t, J=4.4 Hz, 1H), 3.35 (m, 1H), 4.78 (s, 2H).

$^{13}$C NMR (CDCl$_3$): $\delta_c$ 168.4, 94.6, 73.9, 47.3, 46.2, 37.5

Anal. Calc. for C$_6$H$_7$Cl$_3$O$_3$; C 30.87; H, 3.02. Found: C, 31.53; H, 3.15.

EXAMPLE 4

Preparation of the Poly(ethyleneglycol) (PEG) Substrate.

PEG of molecular weight 1300–1600 (Aldrich) was chosen because of its solubility and melting point characteristics.

Very low molecular weight oligomers were removed by the following procedure. To 200 mL of anhydrous isopropyl ether under a dry nitrogen atmosphere were added 25 g of PEG. The mixture was stirred and warmed to about 45° C.

The mixture was held at this temperature for two hours. During this time the polymer melted but formed a separate liquid phase at the bottom of the reaction vessel. Upon cooling to 0° C. in an ice/water bath, the PEG solidified and some dissolved polymer precipitated. The solid PEG was fractured into a relatively fine powder by rapid stirring.

The powder was recovered by filtration, washed with additional cold isopropyl ether, and dried under vacuum at room temperature. The procedure yielded 24.2 g of PEG.

EXAMPLE 5

Resolution of 2,2,2-trichloroethyl (R,S)-3,4-epoxybutanoate (Compound (R,S) 1)

100 mL of anhydrous isopropyl ether were placed in a 300 mL three-necked round bottom flask equipped with a magnetic stirrer and a dry nitrogen inlet. 16 g (11.0 mmol, assuming a molecular weight of 1500) of the previously prepared PEG were added to the flask. The mixture was heated to about 45° C. with stirring. In rapid succession thereafter were added 4.0 g (17.1 mmol) of (R,S) 1 compound and 4.3 g of PPL (35% protein, activity=35–70 units per mg, Sigma) which had been dried for three days in vacuo over phosphorus pentoxide as previously described (Wallace, J. S.; and Morrow, C. J., *J. Polym. Sci. Part A: Polym. Chem.*, 1989, 27, 2553).

After 4.5 hrs, VPC analysis indicated that 50% of the starting ester had been consumed and the reaction was stopped by rapid cooling in an ice/water bath. The PPL and esterified PEG mixture were filtered from the cold mixture and washed with cold isopropyl ether. The filtrate was concentrated by evaporation to yield 1.72 g (86%) of 2,2,2-trichloroethyl (R) (+)-3,4-epoxybutanoate (compound (R)-1).

$[\alpha]_D^{23}$+5.05° (C=4, CHCl$_3$).

The $^1$H and $^{13}$C NMR spectra were identical with those described above for the racemic material.

The recovered PEG and esterified PEG was dissolved in CH$_2$Cl$_2$ and freed of the insoluble PPL enzyme by suction filtration using a fitted glass funnel. The recovery of solid material was 15.82 g (98.9%).

$^1$H NMR (CDCl$_3$): $\delta$3.62 (s) and 2.6 (br s) were strong absorptions arising from the PEG.

$\delta$2.54 (d of d of d), 2.80 (t), 3.25 (m) comprise a weak set of absorptions from the 3,4-epoxybutyrate.

There is no absorption near $\delta$4.8 for the methylene of a trichloroethyl ester.

EXAMPLE 6

Isolation of (S)-3,4-epoxybutanoate as a Methyl Ester

To 100 mL of anhydrous isopropyl ether were added 14.5 g (9.4 mmol) of the recovered PEG and the mixture was stirred and heated to 50° C. In rapid succession, were added to the mixture 8.25 g (0.25 mmol) of anhydrous methanol and 2.2 g of PPL. The reaction was stopped after approximately 30 hours by cooling the reaction vessel in an ice/water bath. The solidified PEG was then collected by filtration and washed with cold isopropyl ether.

The filtrate was concentrated by evaporation to yield 0.91 g (92%) of methyl (S) (−)-3,4-epoxybutanoate.

$[\alpha]_D^{20}$ −11.61° (c=1.8, CHCl$_3$) (Lit. [$\alpha$9 $_D^{r.t.}$: −10.67° (c=1.8, CHClfor the unchanged enantiomer from the enzymatic hydrolysis (Mohr, P.; Rosslein, L.; Tamm, C., *Helv. Chim. Alta*, 1987, 70,142).

The protein NMR spectrum was identical with that described previously (Mohr, P.; Rosslein, L.; Tamm, C., *Helv. Chim. Alta*, 1987, 70,142).

The TLC and VPC behaviors were identical with those of an authentic racemic sample.

EXAMPLE 7

Conversion of 2,2,2-Trichloroethyl-(R)-3,4-Epoxybutanoate (Compound (R)-1) to (R) (−)-Carnitine Chloride (Compound 3)

1.5 g, (6.42 mmol) of 2,2,2-Trichloroethyl (R)-3,4-epoxybutanoate (compound (R)-1) were suspended in 15 mL of 0.1M phosphate buffer that had been adjusted to pH 7.8. To this mixture were added 200 mg of the lipoprotein lipase Amano P from Pseudomonas sp. (AMANO Int'l Enzyme Co., Troy, Va.)

The mixture was stirred at ambient temperature while maintaining the pH near 7.5 by slowly adding 1M aqueous NaOH. After about 4 hours the consumption of base ceased and the reaction mixture was extracted with 2×10 mL of methylene chloride to remove the trichloroethanol that had been freed.

The aqueous solution of (R)-3,4-epoxybutanoate was converted to (R) (−)-carnitine chloride (compound 3) in 72% yield following the method described by Bianchi et al., supra).

$[\alpha]_D^{25°}$ −22.9° (lit. $[\alpha]_D^{25°}$ −23.7°

M. P.: 146° C., decomp. (Lit. 142° C., decomp., (Strack, E.; Lorenz, J. Z., *Physiol. Chem.*, 1960, 318, 129)

$^1$H NMR (D$_2$O): δ2.51 (Strack, E.; Lorenz, J. Z., *Physiol. Chem.*, 1960, 318, 129) (two d of d, 2H), 3.06 (s, 9H), 3.34 (m, 2H), 4.52 (m, 1H).

The enantiomeric excess as determined by comparison of the optical rotation with the literature value was 96.6%.

The carnitine chloride displayed a rotation $[\alpha]_D$ —22.8° corresponding to an enantiomeric excess of 96% by comparison with the literature value of $[\alpha]_D$ —23.7% for the natural product.

EXAMPLE 8

Proof of the Structure and Enantiomeric Purity of the 2,2,2-Trichloroethyl (R)-3,4-Epoxybutanoate by Its conversion to (R)-(−)-Carnitine Chloride The unchanged 2.2.2-trichloroethyl (R)-3,4-epoxybutanoate was converted to the well known (R) (−)-carnitine chloride by enzymatic hydrolysis of the trichloroethyl ester with Amano P enzyme, a nonspecific lipoprotein lipase from Pseudomonas species, followed by treatment with trimethylamine and acidification with HCl as described by Bianchi et al., supra.

The complete hydrolysis of both enantiomers requires only four hours, the same time as was required for Amano P to hydrolyze the pure (R) enantiomer during its conversion to carnitine chloride. Thus, the high enantiomeric purity of this enantiomer is attributable entirely to the selectivity of the PPL during the transesterification by PEG, and not to a double resolution process involving the Amano P.

EXAMPLE 10

Comparison of Stereochemical Purity of Isomers Obtained by the Method of the Invention and a Prior Art Method.

(a) Previously Reported Enzyme-Catalyzed Resolution of 3,4-Epoxybutyrates

The resolution of 3,4-epoxybutyrate by enantioselective enzymatic hydrolysis of the methyl or other alkyl ester was reported by Mohr et al., (Mohr, P.; Rosslein, L.; Tamm, C., *Helv. Chim. Acta,* 1987, 70, 142; Mohr, P.; Rosslein, L.; Tamm, C., *Tetrahedron Lett.,* 1989, 30, 2513) and by Bianchi et al. (Bianchi, D.; Cabri, W.; Cesti, P.; Francalanci, F.; Ricci, M., *J. Org., Chem.,* 1988, 53, 104).

In the former report, the methyl ester was hydrolyzed with pig liver esterase to give 40% recovery of

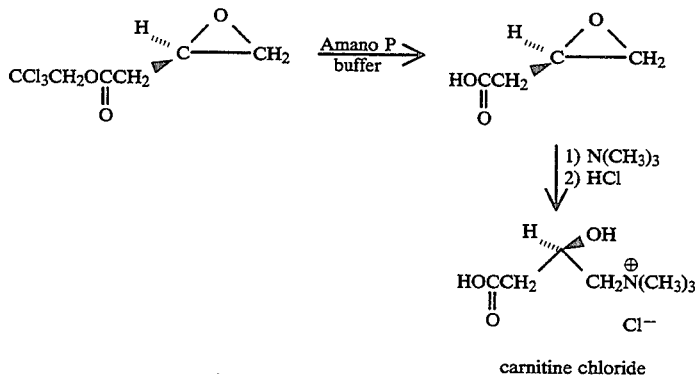

EXAMPLE 9

Evidence Against Improvement in the Enantiomeric Purity of the Unchanged 2,2,2-Trichloroethyl (R)-3,4-Epoxybutanoate during its Enzymatic Hydrolysis Using Amano P Enzyme A survey of 13 different enzyme preparations by Bianchi et al., supra, led to the conclusion that PPL provides the best enantioselectivity during the hydrolysis of 3,4-epoxybutanoates if alkyl (particularly butyl, isobutyl, and octyl) esters are hydrolyzed. An ee of >95% can be achieved for the unchanged (R)-ester if 60–70% of the starting material is hydrolyzed.

Bianchi et al, supra, have shown that the hydrolysis of isobutyl 3,4-epoxybutanoate using Amano P enzyme as the catalyst occurs without stereoselectivity. We have found that the hydrolysis of 2,2,2-trichloroethyl (R,S)-3,4-epoxy butanoate in the presence of Amano P also proceeds without stereoselectivity.

unchanged (R)-ester and a 30% yield of the (S) acid. An enantiomeric excess of 97% was reported for the (S) acid based on its conversion to (+)-gamma-amino-β-hydroxybutyric acid.

The authors established an ee of 82% for the unchanged methyl (R)-3,4-epoxybutyrate ($[\alpha]_D^{22}$+10.67° (c=1.8, CHCl$_3$)) by converting it to methyl (S)-3-hydroxypentanoate and comparing the specific rotation found with that reported for a sample of the opposite enatiomer of the same material. The latter material had been shown optically pure by HPLC analysis of the (S)-α-methoxy-α-trifluoromethylphenylacetate derivative (Mori, K.; and Ikunaka, M., *Tetrahedron*, 1984, 40, 3471).

(b) Optical Purity of the Transesterified Enantiomer by the Method of the Invention The poly(ethylene glycol) ester of (S)-3,4-epoxybutanoate was converted to methyl (S)-3,4-epoxybutanoate by transesterification with methanol using porcine pancrease lipase as the catalyst. The conditions were as follows.

To 100 mL of anhydrous isopropyl ether was added 14.5 g (9.4 mmol) of the recovered PEG ester and the mixture stirred and heated to 50° C. 8.25 g (0.25 mmol) of anhydrous methanol and 2.2 g of PPL were added in rapid succession to the mixture. After approximately 30

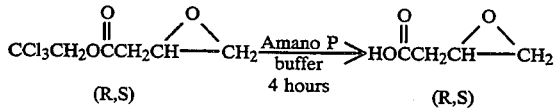

hrs, the reaction was stopped by cooling in an ice/water bath and then the solidified PEG was collected by filtration and washed with cold isopropyl ether. The filtrate was concentrated by evaporation to yield 0.91 g (92%) of methyl (S)-(−)-3,4-epoxybutanoate.

Based on a specific rotation of −10.67° indicating an ee of 82% for methyl (S)-3,4-epoxybutyrate (Mohr, P.; Rosslein, L.; Tamm, C., *Tetrahedron Lett.*, 1989, 30, 2513) the rotation of −11.61° observed for the methyl (S)-3,4-epoxybutanoate isolated from the PEG corresponds to an ee of 89% for that compound.

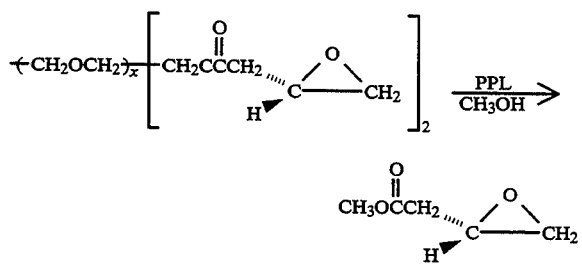

The invention now being fully described, it will be apparent to one of ordinary skill in the art that many changes and modifications can be made thereto without departing from the spirit or scope of the invention as set forth herein.

We claim:

1. A method of separating the stereoisomers of a racemic mixture of a compound of the following formula:

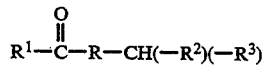

wherein R is selected from the group consisting of a carbon-carbon single bond, $CH_2$, $C_2H_4$, O, $OCH_2$ and $OC_2H_4$; $R^1$ is selected from the group consisting of —OH, —O($C_1$-$C_6$) alkyl, —O($C_2$-$C_{15}$) alkenyl, —O($C_2$-$C_{15}$) alkynyl, —O($C_3$-$C_{15}$) cycloalkyl, and —O($C_6$-$C_{22}$) aryl, all of which groups containing more than one carbon may contain N, S or O in the chain or ring structure, and all of which may be further substituted with one or more ($C_1$-$C_4$) alkyl, OH, $NO_2$ or halogen; $R^2$ is selected from the group consisting of OH, —O($C_1$-$C_{12}$) alkyl, —O($C_2$-$C_{12}$) alkenyl, —O($C_2$-$C_{12}$) alkynyl, ($C_3$-$C_{12}$) cycloalkyl, ($C_3$-$C_{12}$)cycloalkenyl, ($C_4$-$C_{22}$) aryl, ($C_5$-$C_{23}$) alkylaryl and ($C_5$-$C_{23}$) arylalkyl, all of which groups containing more than one carbon may be substituted in the ring or chain with O, N or S; and $R^3$ is selected from the group consisting of the $R^2$ moieties, $NH_2$, $OR^2$, $NHR^2$, $SR^2$, $O(C_1$-$C_6)$ acyl or aroyl, $NH$—($C_1$-$C_6$) acyl or aroyl, —$CH(R^2)$ (—R—$COR^1$) and halogen, provided that $R^3$ is different from $R^2$; or wherein $R^2$ and $R^3$ may form a ring selected from the group consisting of ($C_3$-$C_{12}$) cycloalkyl and ($C_3$-$C_{12}$) cycloalkenyl, each of which may have one or more ring carbons replaced with O, NH or S, said method comprising obtaining a racemic mixture of a reactive ester of the formula

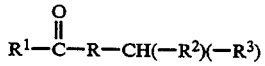

wherein R, $R^1$, $R^2$ and $R^3$ are as defined above;

reacting the reactive ester with a poly(ethylene glycol) of average molecular weight of about 100 to 5,000 Daltons and an enzyme which selectively transesterifies one enantiomer of an ester function which is proximate to a chiral isomeric site, the reactive ester, the poly(ethylene glycol) and the enzyme being reacted in a medium, in proportions and under conditions effective to form a chiral site proximate poly(ethylene glycol) ester, wherein the enzyme is porcine pancreatic lipase; and separating the chiral site proximate poly(ethylene glycol) ester(s) from the reaction medium, the reactive ester, the poly(ethylene glycol) and the enzyme.

2. The method of claim 1, wherein the separation step is conducted by separating the reactive ester and the reaction medium from the enzyme, the excess poly(ethylene glycol) and the poly(ethylene glycol) ester at a temperature where the poly(ethylene glycol) and the poly(ethylene glycol) ester(s) are in solid form or in a separate liquid phase;

separating the excess poly(ethylene glycol) and the poly(ethylene glycol) ester(s) from the enzyme by extracting with a solvent for the poly(ethylene glycol) and the poly(ethylene glycol) ester(s) and separating the solution from the enzyme; and separating the excess and the esterifying poly(ethylene glycol) from the ester(s) by converting the acyl portion of the ester to the corresponding ($C_1$-$C_4$) alkyl ester(s), placing the mixture under conditions effective for the poly(ethylene glycol) to form a solid or a separate liquid phase, and separating the poly(ethylene glycol) phase from the alkyl ester and any solvent in which it is dissolved.

3. The method of claim 2, wherein the poly(ethylene glycol) ester(s) is converted to the corresponding ($C_1$-$C_4$)alkyl ester(s) by adding thereto a ($C_1$-$C_4$)alkanol and the enzyme in a medium under conditions effective to form the ($C_1$-$C_4$)alkyl ester(s).

4. The method of claim 1, wherein the reaction of the reactive ester with the poly(ethylene glycol) and the enzyme is conducted in a nonaqueous medium at a temperature of about 15° to 75° C.

5. The method of claim 1, further comprising subjecting the reactive ester separated from the chiral site proximate poly(ethylene glycol) ester(s) if not stereochemically pure to a further reaction step to form further chiral site proximate poly(ethylene glycol) ester(s) by transesterifying with poly(ethylene glycol) any unreacted chiral site proximate reactive ester; and separating the chiral site proximate poly(ethylene glycol) ester(s) from the reaction medium, the reactive ester, the poly(ethylene glycol) and the enzyme.

6. The method of claim 1, further comprising separating the reactive ester and the reaction medium from the enzyme, the poly(ethylene glycol) and the poly(ethylene glycol) ester(s) at a temperature where the poly(ethylene glycol) and the poly(ethylene glycol) ester(s) are in solid form; and separating the reactive ester from the reaction medium, said reactive ester being substantially in the form of stereochemically pure (S) or (R) site proximate reactive ester.

7. The method of claim 6, wherein the separation of the unchanged enantiomer of the chiral site proximate reactive ester from the reaction mixture is conducted by evaporating the medium.

8. The method of claim 1, wherein the reactive ester is reacted with a poly(ethylene glycol) of average molecular weight of about 1,000 to 5,000 Daltons.

* * * * *